United States Patent [19]

Schade et al.

[11] 4,096,122

[45] Jun. 20, 1978

[54] PROCESS FOR THE PRODUCTION OF POLYESTERS OF 1,4-BUTANEDIOL

[75] Inventors: Gerhard Schade, Witten-Bommern; Hans Melin, Witten, both of Germany

[73] Assignee: Dynamit Nobel Aktiengesellschaft, Troisdorf, Germany

[21] Appl. No.: 599,915

[22] Filed: Jul. 28, 1975

Related U.S. Application Data

[63] Continuation of Ser. No. 341,185, Mar. 14, 1973, abandoned.

[30] Foreign Application Priority Data

Mar. 18, 1972 Germany .............................. 2213259

[51] Int. Cl.² ............................................ C08G 63/18
[52] U.S. Cl. ............................................... 260/75 M
[58] Field of Search ........................... 260/75 M, 47 C

[56] References Cited

U.S. PATENT DOCUMENTS

| 3,070,575 | 12/1962 | Cramer | 260/47 |
| 3,635,899 | 1/1972 | Doerr et al. | 260/75 |
| 3,859,257 | 1/1975 | Schade et al. | 260/75 M |

FOREIGN PATENT DOCUMENTS

| 775,030 | 5/1957 | United Kingdom | 260/75 |
| 1,189,262 | 4/1970 | United Kingdom | 260/75 |

OTHER PUBLICATIONS

Goodman et al., Polyesters and their Applications, Reinhold, New York, 1956, pp. 201–202.

Primary Examiner—Lester L. Lee
Attorney, Agent, or Firm—Burgess, Dinklage & Sprung

[57] ABSTRACT

A process for producing a linear polyester which comprises:
(1) condensing excess 1,4-butanediol with a lower alkyl ester of an aromatic dicarboxylic acid at a temperature of less than 200° C;
(2) removing uncondensed 1,4-butanediol therefrom so that the reaction mixture contains no more than 1% by weight 1,4-butanediol;
(3) condensing the so-formed dicarboxylic acid-bis-(4-hydroxy butyl ester) and any oligomer thereof with a dicarboxylic acid at a temperature of 200 to 250° C, the dicarboxylic acid being present in no more than a stoichiometric amount; and
(4) polycondensing the resultant condensate by heating the same at between 250° and 310° C in a vacuum.

20 Claims, No Drawings

PROCESS FOR THE PRODUCTION OF POLYESTERS OF 1,4-BUTANEDIOL

This is a continuation of application Ser. No. 341,185, filed Mar. 14, 1973 and now abandoned.

BACKGROUND OF THE INVENTION

1. FIELD OF THE INVENTION

This invention relates to a process for the production of polyesters from an aromatic dicarboxylic acid component and 1,4-butanediol. More particularly, this invention is directed to the preparation of a linear polyester wherein the quantity of 1,4-butanediol employed in the polymerization is substantially smaller than the quantities heretofore employed. The process of the present invention overcomes some of the known drawbacks connected with prior art polymerization processes.

2. DISCUSSION OF THE PRIOR ART

The use of 1,4-butanediol for the production of polyesters has been known for a long time. The dicarboxylic acid condensed-in may be both an aliphatic and an aromatic dicarboxylic acid. In the event that the polyesters contain condensed therein only aliphatic dicarboxylic acids in addition to 1,4-butanediol, products are obtained which, in practice, have not gained any major importance since their melting and/or softening points are extremely low. On the other hand, polyesters of 1,4-butanediol and aromatic dicarboxylic acids such as terephthalic acid, isophthalic acid, etc., possibly in admixture with aliphatic dicarboxylic acids such as adipic acid, sebacic acid, dimeric fatty acids, etc., are of economic importance, e.g., as fusion bonding agents, as raw materials for the production of coatings according to the known powder coating processes, for the production of rubber-elastic block polycondensates. Some polyesters of this type are described, for instance, in the French Pat. No. 1,441,060 or in the U.S. Pat. No. 3,423,281.

Thus far, these polyesters have generally been made in two stages, analogous to the processes that are customarily applied for the production of polyethylene terephthalate. In these processes, the mixture of the aromatic dicarboxylic acids and/or lower alkyl esters of these dicarboxylic acids is first reacted in the melt at temperatures above 200° C with at least a 50% molar excess of 1,4-butanediol and then the excess 1,4-butanediol is removed by distillation by means of further temperature increase and subsequent application of a vacuum until the molar ratio of the radicals of the dicarboxylic acids to those of the 1,4-butanediol in the reaction product has become approximately 1:1. This molar ratio means that a polyester of high molecular weight has been produced.

But this process has the following drawbacks: At the high temperatures prevailing during condensation considerable quantities of tetrahydrofuran and water are continuously produced, which have to be distilled off as well. Therefore, the distiller-off 1,4-butanediol is contaminated and cannot be reused directly. The working-up of the 1,4-butanediol/tetrahydrofuran/water mixture by distillation is very difficult and large amounts of 1,4-butanediol are lost.

It is therefore of considerable economic significance to modify the process outlined above for the production of polyesters containing condensed therein 1,4-butanediol in such a way that the aforementioned drawbacks do not arise. The obvious solution, i.e., to reduce the excess of 1,4-butanediol used, entails the following difficulties:

As is well-known, it is impossible in the analogous production of polyethylene terephthalate to use a quantity of less than approximately 1.5 moles of ethylene glycol to 1 mole of dialkyl terephthalate while maintaining the usual catalyst concentrations (ranging between $10^{-4}$ and $10^{-4}$ moles/mole of ester) if the ester-interchange reaction is to proceed to an extent that polyesters of sufficiently high molecular weight are obtained in a reproducible manner in the subsequent polycondensation reaction. If the above specified catalyst concentration is increased to such a marked degree that the quantity of ethylene glycol used can be reduced further with respect to a reproducible polycondensability of the starting materials, technically worthless polyesters are obtained, containing large amounts of cross-linked constituents, having low thermal stabilities and showing, as a rule, strong discolorations.

A process has been described for the production of polytetramethylene sebacate by ester-interchange between 1 mole of dimethyl sebacate and only 1.1 mol of 1,4-butanediol, in which temperatures between 172° and 215° C are used throughout and a vacuum is applied (C. S. Marvel, J. H. Johnson, J. Am. Chem. Soc. 72 (1950), 1674). However, with $9 \cdot 10^{-1}$ mole/mole of ester the catalyst concentration is higher by 1 to 3 powers of ten than customary, which, on the basis of the above, must result in extensive thermal decompositions and cross-linkings at higher temperatures than those used of max. 215° C. In those cases in which the polycondensate contains condensed therein aromatic dicarboxylic acids as well, temperatures around only 215° C cannot be maintained either because of the melting point of more than 215° C of the polyester to be produced or as a result of too high a melt viscosity so that this method can be used only specifically for the production of polytetramethylene sebacate and cannot be applied to the production of polyesters containing aromatic dicarboxylic acids condensed therein.

SUMMARY OF THE INVENTION

The limitations and drawbacks of the above-described known processes for the production of linear polyesters of predominantly aromatic dicarboxylic acids and 1,4-butanediol are eliminated, in accordance with the present invention, which tolerates substantially less 1,4-butanediol excess while allowing the production of polyesters having substantially the same properties as the products prepared by the above-described procedures. In accordance with this invention there is provided a process for the production of a linear polyester which comprises:

(1) condensing excess 1,4-butanediol with a lower alkyl ester of an aromatic dicarboxylic acid at a temperature of less than 200° C;
(2) removing uncondensed 1,4-butanediol therefrom so that the reaction mixture contains no more than 1% by weight 1,4-butanediol;
(3) condensing the so-formed dicarboxylic acid bis-(4-hydroxy butyl ester) and any oligomer therein with a dicarboxylic acid at a temperature of 200° to 250° C, the dicarboxylic acid being present in no more than a stoichiometric amount relative to the dicarboxylic acid-bis-(4-hydroxy butyl ester); and (4) polycondensing the resultant condensate by heating the same at between 250° and 310° C in a vacuum.

In accordance with the present invention, excess 1,4 butanediol is initially reacted with a lower alkyl ester of an aromatic dicarboxylic acid. Preferably the 1,4-butanediol is present in a molar ratio of 1.05 to 1.25, based upon the sum of the lower alkyl esters of aromatic dicarboxylic acids and free aromatic or aliphatic dicarboxylic acids. Suitably, lower alkyl esters of aromatic dicarboxylic acid are dimethyl isophthalate, dimethyl terephthalate or the like. Transesterification takes place at a temperature of less than 200° C, preferably between 160° and 190° C. This reaction is carried out at atmospheric pressure.

After the transesterification is complete, uncondensed 1,4-butanediol if present is removed suitably by heating the reaction mixture and applying a vacuum thereto. Generally the vacuum can be between 10 and 100 Torr but the temperature is maintained not above 200° C, preferably between 180° and 200° C. Removal of the 1,4-butanediol is effected so that the resultant reaction mixture contains no more than 1% by weight butanediol, and optimumly no free 1,4-butanediol.

The initial transesterification and removal of uncondensed 1,4-butanediol effects the formation of an intermediate dicarboxylic acid-bis-(4 hydroxy butyl ester) or oligomers thereof. These intermediates are thereafter esterified with a dicarboxylic acid which may be one other than the acid of the ester employed in the initial precondensation step. This condensation is carried out at a temperature of between 200° and 250° C, the dicarboxylic acid being present in no more than a stoichiometric amount relative to the dicarboxylic acid-bis-(4-hydroxybutyl ester) and/or oligomers thereof. This second condensation can be suitably carried out at a pressure of between 760 and 10 mm, preferably between 150 and 50 mm. The free dicarboxylic acid is present in a sub-stoichiometric amount, i.e., in an amount of less than 1 mole per mole of dicarboxylic acid-(4-hydroxybutyl ester) and/or oligomers thereof. This esterification is carried out until at least 70% of the carboxylic groups, are esterfied, preferably employing a molar ratio of dicarboxylic acid to the initially employed dicarboxylic acid-(alkyl ester) of between 0.2 and 0.8. Thereafter the so treated precondensate is subjected to poly-condensation by heating the reaction mixture in the melt to effect melt condensation, the heating being carried out at a temperature between 250° and 310° C, suitably in a vacuum, such that the pressure is between 2 and 0.1 Torr. This latter polycondensation is carried out until the desired mole weight is obtained.

DESCRIPTION OF SPECIFIC EMBODIMENTS

The feasibility of the above-described process could not be predicted for two reasons:

(1) From kinetic investigations, Hovenkamp and Munting (from: Reprints, Vol. I, pp. 119-122, of the IUPAC International Symposium on Macromol Chemistry, Budapest, 1969) concluded that, in the case of the polyethylene terephthalate preparation, the diglycol formation, which theoretically corresponds to the tetrahydrofuran formation, takes place proportionally to the hydroxyl group concentration in the reaction mixture, whereby the origin of the hydroxyl groups is of no importance regarding the ether formation whether or not free diol is present. Since, in the extreme case, the dicarboxylic-bis-(4-hydroxybutyl ester) has a comparatively large content in hydroxyl groups, it could not be expected that it would be possible to heat this compound to more than 200° C without initiating a noteworthy tetrahydrofuran formation.

(2) Moreover, it had to be expected that water produced in the esterification reaction would hydrolyze already existing ester groups and thereby form new 1,4-butanediol which turns into tetrahydrofuran under the esterification conditions at temperatures of more than 200° C.

As will be easily understood from the above, the process is limited to those cases in which the molar ratio of the dicarboxylic acids used to the dicarboxylic acid dialkyl esters used is 1 at the most, since at the most 1 mole of dicarboxylic acid-bis(4-hydroxybutyl ester) can be esterified with 1 mole of dicarboxylic acid to produce polymers of high molecular weight, excluding the presence of free 1,4-butanediol. In practice it is advisable to limit the molar ratio to 0.8 at the most in order to be certain to retain a sufficient hydroxyl group excess for the polycondensation reaction.

The first stage of the process according to the invention, the ester-interchanges of lower alkyl esters of aromatic dicarboxylic acids, is carried out at temperatures of less than 200° C with an excess of 1,4-butanediol. The quantity of 1,4-butanediol used in the entire reaction is sufficient to obtain a molar ratio of 1,4-butanediol to the sum of the lower alkyl esters of aromatic dicarboxylic acids used and the free dicarboxylic acids used amounting to 1.05 - 1.25, preferably 1.1 - 1.2. The dialkyl esters used have an aromatic dicarboxylic acid radical and $C_{1-6}$ alkyl radicals. The methyl esters of isophthalic acid or terephthalic acid are preferred.

As catalysts the known ester-interchange catalysts can be used such as carboxylates, hydroxides, oxides, alcoholates, glycolates or organic complex compounds of zinc, manganese, cobalt, lead, calcium, cerium and the alkali compounds, if these compounds are soluble in the reaction mixture. They are used in a concentration of $10^{-2}$ to $10^{-4}$ mole/mole of dicarboxylic acid ester.

It is advantageous to render the ester-interchange catalysts ineffective following the completion of the ester-interchange by means of known inhibitors, in particular phosphorus compounds such as phosphoric acid, phosphorous acid, hypophosphorous acid, phosphinic acid, phosphoric acids, their alkyl or aryl esters or salts in order to increase the thermal stability of the polyesters.

The ester-interchange reaction takes place at temperatures of less than 200° C, preferably at 160° - 190° C. At the end of the ester-interchange, a vacuum preferably is applied in order to remove the unreacted butanediol if present by distillation at temperatures of less than 200° C.

In a second stage the dicarboxylic acid-bis-(4-hydroxybutyl ester) obtained in this manner and its possibly produced oligomers are esterified with free dicarboxylic acid. The dicarboxylic acids may be aromatic or aliphatic dicarboxylic acids, in particular, isophthalic acid, terephthalic acid or $C_{3-10}$-alkyl dicarboxylic acids, in particular, adipic acid, azelaic acid or sebacic acid. In this operation, the molar ratio of dicarboxylic acid to the initially employed dicarboxylic acid ester — is 0.8 at the most. The esterification is carried out at temperatures of 200° - 250° C, preferably 210° - 240° C, the application of a vacuum of approximately 50 - 150 Torr considerably reducing the residence time in the reaction mixture of water released as a result of condensation so that undesirable secondary reactions are avoided to a large extent. Therefore, the esterification reaction is carried out preferably under reduced pressure.

If, however, the molar ratio of dicarboxylic acid to dicarboxylic acid dialkyl ester is less than 0.2 and the molar ratio of the butanediol to the sum of these acid components is equal to or more than 1.2, it is not necessary to apply a vacuum during esterification since, in that case, the concentration of interfering cleavage and by-products is low enough in order not to jeopardize the success of the subsequent polycondensation reaction. The conditions under which it is not necessary to apply a vacuum, are however largely dependent upon the specific apparatus used, e.g., possibility of overheating the reaction mixture at the reactor wall, agitation intensity and degree of filling the reactor, and can therefore not be generaly specified.

To catalyze the esterification and the subsequent polycondensation, known esterification and polycondensation catalysts are added such as compounds, soluble in the reaction mixture, of antimony, titanium, arsenic, bismuth, tin, germanium and lanthanum, in quantities of approximately $10^{-2}$ to $10^{-4}$ mole per mole of the reaction components. The esterification catalyst can be added to the starting compounds, together with the ester-interchange catalyst.

The opportunity of applying temperatures of more than 200° C to esterify the dicarboxylic acid with the ester-interchange mixture results in extremely short esterification times, above all since it suffices to react approximately 75% of the introduced carboxyl groups in the esterification stage, while the esterification of the remaining carboxyl groups can be left to the polycondensation stage. In the event that the dicarboxylic acids to be esterified are of the type that is difficultly soluble in the ester-interchange mixture such as isophthalic acid, the esterification reaction can be terminated as soon as a clear melt has been obtained. If dicarboxylic acids are used that are soluble in the reaction mixture, either reaction temperatures and periods can be utilized, which are appropriate for the reaction with isophthalic acid, or the water-splitting reaction can be followed analytically. The maintenance of a constant degree of esterification at the end of the esterification stage does not have any noticeable effect on the course of the polycondensation at 250° -310° C in a vacuum in the third stage and, thus, on the properties of the product and is therefore of minor critical importance.

The tetramethylene dicarboxylic acid polyesters produced by this method are suprisingly of excellent quality although the concentration of 1,4-butanediol used was reduced compared to the hiterto known processes without increasing the catalyst concentration. They are colorless or only very slightly colored, thermally stable and exhibit only a very slight or no drop in viscosity on heating in the melt for a lengthy period of time. Compared to the customary mode of operation, the total reaction time is considerably shorter in the process according to the invention. If, however, contrary to the process according to the invention, it is worked in accordance with the known processes in such a way that, with the use of 1 to 1.25 moles of 1,4-butanediol/mole of dicarboxylic acid and its esters, the temperature is increased to more than 200° C — e.g., to 220° to 240° C — before the unreacted butanediol is removed to a large extent at least, polycondensates are obtained in the polycondensation that either have an insufficiently high molecular weight or are thermally very unstable and contaminated by decomposition products.

The following example may be modified in any way desired with respect to the dicarboxylic acids used and/or its esters and the thus modified polyesters may be adapted in this manner to their application. This modification does not affect the success of the polycondensation reaction itself.

In order to more fully illustrate the nature of the invention and the manner of practicing the same, the following example is presented.

EXAMPLE 67.9 g dimethyl terephthalate (0.35 mole), 49.5 g 1,4-butanediol (0.55 mole), 0.035 g zinc acetate dihydrate and 0.03 g butyltitanate were stirred for 1 hour at 160° - 190° C, yielding 27 milliliters of methanol (approximately 96% of theory). Thereupon a vacuum of 50 Torr was applied at 190° C; after about 15 minutes no further development of butanediol vapors was observed. Thereupon 24.9 g isophthalic acid (0.15 mole) and 0.056 g triphenyl phosphite were added at 190° C in countercurrent to a stream of nitrogen, a vacuum of approximately 100 Torr was applied and the temperature was increased within 30 minutes from 190° to 230° C, which yielded a clear, colorless melt. Subsequently the temperature was increased to 270° C within 30 minutes and the pressure was reduced simultaneously to 0.2 Torr. Following another 30 minutes under the specified end conditions a relative viscosity of 1.83 was attained, which was determined in a one percent by weight polymer containing solution in a mixture of 60% by weight of phenol and 40% by weight of 1,1,2,2-tetrachloroethane at 25° C. The total reaction time was 2¾ hours. The relative viscosity was determined in accordance with W. R. Sorenson and T. W. Campbell, *Preparative Methods of Polymer Chemistry*, Interscience Publishers, Inc., New York, 1961, pp. 38-40.

What is claimed is:

1. A process for producing a linear polyester which consists essentially of:
   (1) reacting in the presence of an ester interchange catalyst an excess of 1,4-butanediol with a lower alkyl ester of an aromatic dicarboxylic acid at a temperature of less than 200° C;
   (2) removing at a temperature not above 200° C unreacted 1,4-butanediol therefrom so that the reaction mixture contains no more than 1% by weight 1,4-butanediol by applying a vacuum thereto;
   (3) adding to the reaction mixture from step (2) dicarboxylic acid and reacting the resultant mixture at a temperature of 200°-250° C, the dicarboxylic acid being present in no more than a stoichiometric amount relative to any dicarboxylic acid-bis-(4-hydroxybutyl ester) and/or oligomers thereof which are formed during step (1) and being such that the mol ratio of 1,4-butanediol employed in step (1) to the sum of the mols of the lower alkyl esters of aromatic dicarboxylic acid in step (1) and the mols of dicarboxylic acid added in step (3) is between 1.05 and 1.25; and
   (4) polycondensing in the presence of a polycondensation catalyst the resultant esterification product by heating the same at between 250° and 310° C in a vacuum.

2. A process according to claim 1 wherein the molar ratio of dicarboxylic acid to the iinitially employed dicarboxylic acid ester is no more than 0.8.

3. A process according to claim 1 wherein the unreacted 1,4-butanediol is removed by heating the transesterification products at a temperature between 180° and 200° C under a vacuum of between 10 and 100 Torr.

4. A process according to claim 1 wherein the molar ratio is between 1.1 and 1.2.

5. A process according to claim 2 wherein the dicarboxylic acid and the dicarboxylic acid-bis-(4-hydroxybutyl ester) and/or oligomers thereof are heated at a temperature between 200° and 250° C.

6. A process according to claim 5 wherein the dicarboxylic acid and dicarboxylic acid-bis-(4-hydroxybutyl ester) and/or the oligomers thereof are heated while the vacuum on the reaction mixture is between 50 and 150 Torr.

7. A process according to claim 1 wherein said aromatic dicarboxylic acid ester is selected from the group consisting of terephthalic and isophthalic acid alkyl esters, the alkyl group is between 1 and 6 carbon atoms and the dicarboxylic acid employed in step 3 is an aromatic or aliphatic dicarboxylic acid.

8. A process according to claim 7 wherein the dicarboxylic acid emplpoyed in step 3 is selected from the group consisting of isophathalic acid, terephthalic acid and $C_{3-10}$ alkyl dicarboxylic acid.

9. A process according to claim 8 wherein said acid is adipic, azelaic or sebacic.

10. A process according to claim 1 wherein the first step is carried out in the presence of a catalyst which is a carboxylate, hydroxide, oxide, alcoholate, glycolate or organic complex of zinc, manganese, cobalt, lead, calcium, cerium or alkali metal, the catalyst being present in a concentration of $10^{-2}$ to $10^{-4}$ mol per mol of dicarboxylic acid ester.

11. A process according to claim 10 wherein after the transesterification product from step 1 is formed, there is introduced into the reaction mixture an ester interchange inhibitor selected from the group consisting of phosphoric acid, phosphorous acid, phosphorous and hypophosphorous acid, phosphinic acid, phosphoric acid, phosphoric acid alkyl ester and phosphoric acid aryl ester and phosphoric acid salt.

12. A process according to claim 1 wherein the dicarboxylic acid added in step (3) is an aromatic dicarboxylic acid.

13. A process according to claim 12 wherein said acid is selected from the group consisting of isophthalic acid and terephthalic acid.

14. A process according to claim 1 wherein prior to step (3) there is introduced into the reaction mixture an ester-interchange catalyst inhibitor selected from the group consisting of phosphoric acid, phosphorous acid, hypophosphorous acid, phosphinic acid, alkyl esters of phosphoric acid, aryl esters of phosphoric acid and phosphoric acid salts.

15. A process according to claim 13 wherein:
A. The transesterification of step (1) is carried out at a temperature of 160° to 190° C at atmospheric pressure;
B. The unreacted butanediol is removed, according to step (2), by applying a vacuum thereto at 10–100 Torr;
C. The esterification of step (3) is carried out until at least 70% of the carboxylic groups are esterified, said esterification being carried out at a pressure of 10–760 mm pressure; and
D. The polycondensation of step (4) is carried out at a pressure of 0.1 to 2 Torr.

16. A process according to claim 15 wherein the removal step of step (2) is conducted until the reaction mixture is free of butanediol.

17. A process according to claim 15 wherein the esterification of step (3) is carried out at a pressure of 50 to 150 mm.

18. A process according to claim 13 wherein the mol ratio of acid added in step (3) to aromatic dicarboxylic acid ester of step (1) is not in excess of 1.

19. A process according to claim 13 wherein the mol ratio of acid added in step (3) to aromatic dicarboxylic acid ester of step (1) is not in excess of 0.8.

20. A process according to claim 13 wherein the mol ratio of acid added in step (3) to aromatic dicarboxylic acid ester of step (1) is not in excess of 0.2, the mol ratio of butanediol to the sum of the mols of the lower alkyl ester of aromatic dicarboxylic acid in step 1 and the mols of dicarboxylic acid added in step (3) is at least 1.2 and the condensation of step (3) is carried out at atmospheric pressure.

* * * * *

UNITED STATES PATENT AND TRADEMARK OFFICE
CERTIFICATE OF CORRECTION

PATENT NO. : 4,096,122
DATED : June 20, 1978
INVENTOR(S) : Schade et al

It is certified that error appears in the above-identified patent and that said Letters Patent are hereby corrected as shown below:

Column 1, line 60, "distiller" should read -- distilled --.

Column 2, line 9, "$10^{-4}$" first occurrence should read -- $10^{-2}$ --.

Column 5, line 17, "generaly" should read -- generally --.

Column 6, line 67, "iinitially" should read -- initially --.

Signed and Sealed this

Sixteenth Day of January 1979

[SEAL]

Attest:

RUTH C. MASON
Attesting Officer

DONALD W. BANNER
Commissioner of Patents and Trademarks